(12) United States Patent
Reynolds et al.

(10) Patent No.: US 8,523,807 B2
(45) Date of Patent: Sep. 3, 2013

(54) AIRLESS MIXING WITH A BY-PASS SYRINGE

(75) Inventors: David L. Reynolds, Bromont (CA); Daniel MacDonald, Bromont (CA); Roger McCarthy, Brigham (CA)

(73) Assignee: Duoject Medical Systems Inc., Bromont, Quebec (CA)

( * ) Notice: Subject to any disclaimer, the term of this patent is extended or adjusted under 35 U.S.C. 154(b) by 937 days.

(21) Appl. No.: 12/009,783

(22) Filed: Jan. 22, 2008

(65) Prior Publication Data

US 2008/0188828 A1 Aug. 7, 2008

(30) Foreign Application Priority Data

Jan. 22, 2007 (CA) .................................. 2,574,746

(51) Int. Cl.
*A61M 37/00* (2006.01)
(52) U.S. Cl.
USPC .............................................. 604/88; 604/82
(58) Field of Classification Search
USPC ............ 604/82–92, 135, 181, 182, 184–187, 604/190, 200, 201, 224, 232–236, 520
See application file for complete search history.

(56) References Cited

U.S. PATENT DOCUMENTS

| 4,465,478 | A | * | 8/1984 | Sabelman et al. | 604/224 |
|---|---|---|---|---|---|
| 4,821,738 | A | * | 4/1989 | Iwasaki et al. | 600/578 |
| 5,067,948 | A | * | 11/1991 | Haber et al. | 604/213 |
| 5,176,642 | A | * | 1/1993 | Clement | 604/135 |
| 5,334,162 | A | * | 8/1994 | Harris | 604/232 |
| 5,378,233 | A | * | 1/1995 | Haber et al. | 604/83 |
| 5,637,100 | A | * | 6/1997 | Sudo | 604/238 |
| 5,971,953 | A | * | 10/1999 | Bachynsky | 604/90 |
| 2003/0236497 | A1 | * | 12/2003 | Fremming et al. | 604/126 |

FOREIGN PATENT DOCUMENTS

WO   WO 96/26754   * 9/1996

OTHER PUBLICATIONS

"cap." Merriam-Webster Online Dictionary. 2010. Merriam-Webster Online. <http://www.merriam-webster.com/dictionary/cap>.*

* cited by examiner

*Primary Examiner* — Kami A Bosworth
(74) *Attorney, Agent, or Firm* — Eric Fincham (57) ABSTRACT

A transfer and mixing device which utilizes a by-pass cartridge and a syringe. After mixing the dry component and the diluent in the by-pass cartridge, the mixture can be passed to a syringe which includes a syringe plunger having a fluid passageway therein with a hydrophobic membrane covering the passageway. The mixture can be transferred back and forth between the by-pass cartridge and the syringe through a small bore to achieve mixing, particularly in the case of microspheres held in suspension.

17 Claims, 6 Drawing Sheets

AIRLESS MIXING WITH A BY-PASS SYRINGE

FIELD OF THE INVENTION

The present invention relates to improvements in syringes and in particular, relates to an improved syringe wherein two or more substances are mixed and also to a method for the mixing of two or more substances in a syringe.

BACKGROUND OF THE INVENTION

In pharmaceutical delivery systems, it is often required that a drug in powder form be mixed with a diluent in order to be able to deliver the drug to a patient. To date, this is frequently done by injecting the diluent into a vial containing the powder drug, mixing the drug with the diluent and then aspirating the drug in fluid form into a syringe for subsequent injection into the patient. A manual mixing such as this can be cumbersome and inconvenient and can also lead to wastage of some of the drug which may remain in the vial.

Other more automated systems for mixing the drug and diluent have been developed and are shown in U.S. Pat. Nos. 5,817,055 and 5,716,338. In these patents, the mixing of the drug and diluent is achieved in what is known as a by-pass syringe having two compartments; one containing the drug and the other the diluent.

These devices have been used for many years to aseptically package lyophilized or "freeze-dried" medications together with their diluents. In recent years specially coated drug micro-units have been produced in the form of microspheres which release slowly into the bloodstream when administered are also now being packaged in these devices. The packaging of lyophilized drugs requires that the liquid drug admixture be filled into the top chamber so that once frozen, all water will sublimate under vacuum leaving a dried cake of residual drug product. For this reason an aqueous diluent needs to be filled in the lower chamber of the syringe after the freeze drying cycle. The production of powdered products such as microspheres requires that the diluent be filled in the lower chamber first followed by powder filling in the upper chamber. This will ensure that the diluent is well sealed before entering the well isolated powder-filling environment where unwanted powder contamination is a concern.

The preparation for administration in these double chamber by-pass syringes however is much the same and requires that the device always be held vertically with the exit nozzle pointing upwards. The mixing action occurs when the rear plunger is pushed forward very slowly. This movement can be dampened by using a threaded plunger rod so that the user must screw the rod thereby providing a slow controlled upward movement of the rear plunger. This movement moves the entire diluent including the upper plunger upwards into the by-pass area (any fast uncontrolled movement would move the plunger beyond the by-pass area and block flow of the diluent). Continued slow upward movement will cause all of the diluent to flow through the by-pass around the upper plunger and into the upper chamber mixing with drug component and expelling some of the air above it.

At this point the user must stop pressure on the plunger rod and begin swirling or shaking the syringe to ensure dissolution or suspension of the drug. If either component of the admixture contains a surface active agent to promote wetting then excessive foaming can be a problem as well as the problem of entrained air bubbles. After some time and when the admixture is suitably mixed, and foam or bubbles have been allowed to dissipate, then the user can slowly push the plunger rod to expel the air above the drug surface, attach a needle and inject the medication.

Quite apart from the above, there may also be a requirement to remix a mixture which has separated out and needs to be transferred to a syringe type structure.

SUMMARY OF THE INVENTION

It is an object of the present invention to provide a by-pass type syringe which has a venting structure to permit the expelling of air therefrom.

It is a further object of the present invention to provide a syringe wherein mixing is accomplished by passing the components back and forth through a relatively small opening to subject the mixture to a shearing action.

It is a further object of the present invention to provide a method for mixing two substances in a syringe structure.

According to one aspect of the present invention, there is provided a transfer and mixing device comprising an outer housing, a by-pass cartridge having a by-pass formed therein, the by-pass cartridge being mounted within the outer housing, a septum located at a front end of the by-pass cartridge, a first plunger located at a rear end of the by-pass cartridge, a second plunger located intermediate the septum and the first plunger, the second plunger being located rearwardly of the by-pass, a syringe socket at a front end of the outer housing, the syringe socket including a piercing member extending inwardly towards the septum, a syringe securable to the syringe socket, a syringe plunger mounted in the syringe, the syringe plunger having a fluid passageway therein, a hydrophobic membrane covering the passageway, the passageway thereby permitting the passage of gas therethrough, and a plunger rod.

According to a further aspect of the invention, there is provided a method of mixing a pharmaceutical mixture contained within a container, the container having a plunger located proximate a rear end thereof and a fluid outlet located at a front end thereof, the method comprising the steps of providing a syringe, the syringe having a syringe plunger, a fluid passageway extending through the plunger, and a hydrophobic membrane extending across the fluid passageway, pushing the plunger of the container to cause the mixture therein to pass through a bore communicating with the syringe plunger such that air is expelled through the hydrophobic membrane, and the mixture passes into the syringe, and subsequently pushing the syringe plunger such that the mixture passes back through the bore extending between the fluid passgeway and the container, the bore being sized to provide a mixing action to the pharmaceutical mixture passing therethrough.

According to a still further aspect of the invention, there is provided a method of transferring and mixing a pharmaceutical mixture, the method comprising the steps of supplying a first device comprising an outer housing, a by-pass cartridge having a by-pass formed therein, the by-pass cartridge being mounted within the outer housing, a septum located at a front end of the by-pass cartridge, a first plunger located at a rear end of the by-pass cartridge, a second plunger located intermediate the septum and the first plunger, the second plunger being located rearwardly of the by-pass, a syringe socket at a front end of the outer housing, the syringe socket including a piercing member extending inwardly towards the septum, a first compartment having a pharmaceutical substance therein being defined between the septum and the second plunger, a second compartment having a diluent therein being defined between the first and second plungers, securing a syringe to the syringe socket, the syringe having a syringe plunger mounted therein, the syringe plunger having a fluid passageway therein, a hydrophobic membrane covering the passage, the hydrophobic membrane permitting the passage of gas therethrough, securing a plunger rod to the first plunger at the rear end of the by-pass cartridge, advancing the first plunger to thereby cause the second plunger to move to the by-pass and permit the diluent in the second compartment to mix with the substance in the first compartment to thereby form a mixture, exerting a continued pressure on the plunger rod to cause air to advance from the first compartment to the syringe and through the hydrophobic membrane, exerting a continuing pressure on the plunger rod such that the mixture from the first compartment passes through the piercing member into the syringe, and using a plunger to move the syringe plunger to retransfer the mixture into the first compartment of the by-pass cartridge.

As used herein, the term "container" includes any type of vessel having a cavity therein designed to receive one or more substances. Generally, the container will have an inlet/outlet at opposed ends thereof. The word container will thus include, in the preferred embodiments, various types of syringes and/or cartridges.

Also, as used herein, the term "mixture" will refer to the combination of two or more ingredients, the combination being in the form of a mixture, suspension, admixture, solution, emulsification, etc. In the preferred embodiments, the mixture of the present invention will be a suspension of microspheres and a diluent.

The by-pass cartridge referred to above may be any suitable type of by-pass cartridge which is well-known in the art. Thus, various types of by-pass cartridges have been employed including those having multiple by-passes.

A device for transferring a diluent to a dry pharmaceutical component by means of a by-pass cartridge is well known. Generally, the device will include plungers which form two different storage compartments. A centrally located plunger usually divides the dry pharmaceutical component in the front of the by-pass cartridge and a diluent or liquid component in the rear compartment. A pressure is exerted on a plunger (typically by attachment of a plunger rod thereto) and the rearward plunger is advanced forwardly which will cause pressure to be exerted on the centrally located plunger which will then advance to the location where the diluent can transfer to the front compartment for mixing with the dry pharmaceutical component.

One problem which can arise is that the rear plunger is advanced too rapidly such that it will "overshoot" the by-pass formed in the cartridge and thus render it impossible for the diluent to reach the front compartment. It has been proposed in the art to use a screwthreaded motion to slow down the advancement to overcome this problem.

In one aspect of the present invention, there is provided a rack and pinion arrangement which will also achieve a greater control over advancement of the plungers. This arrangement, as will be discussed in greater detail hereinbelow, permits the operator to exert a slow even force on the plungers such that the centrally located plunger will advance to the by-pass area in a controlled fashion.

In one aspect of the present invention, there is provided an activation cap which permits the by-pass cartridge to be advanced such that it will be pierced by a piercing member located at the front end of the outer housing. This piercing member will include a bore extending therethrough such that a fluid passageway extends from interiorly of the by-pass cartridge through the syringe.

The syringe which is securable to the syringe socket may do so by means of a luer fitting which is well-known in the art. The syringe includes a plunger therein with the plunger preferably located at the front end of the syringe. The plunger is characterized by having a fluid passageway therethrough, with the fluid passageway having a hydrophobic membrane therein. The hydrophobic membrane may be formed of any suitable material such as a polytetrafluoroethylene (PTFE) or Tyvec or similar materials such as PFA, PFEP, PVDA, polysulfone, nylon, etc. Such hydrophobic membranes permit the passage of air therethrough while it has been found that even with moderate pressure on the hydrophobic material, liquid will not pass therethrough while the air within the compartment is expelled.

Thus, there is provided a mixing wherein frothing or the entrainment of air bubbles within the liquid is prevented.

Naturally, it will be understood that other venting structures may be employed if so desired. Thus, one could provide a venting structure on one of the walls defining the mixing compartment.

Preferably, the syringe plunger will not have means for accepting attachment to a plunger rod, though the plunger rod will be utilized. This will prevent any reverse pressure or aspiration which would permit the entry of air into the mixing compartments.

According to the method of one embodiment of the present invention, the first plunger located at the rear end of the by-pass cartridge has a plunger rod attached thereto. Subsequently, the diluent from the rear compartment is advanced through the by-pass to the front compartment where the two components are mixed together. Air will still occupy the upper portion of the first compartment.

Subsequently, the mixture is transferred through the piercing member into the syringe. Continued advancement of the plungers in the by-pass cartridge will cause the mixture to advance into the syringe. Air above the mixture will be expelled through the hydrophobic membrane. As a result, an airless mixture is achieved.

Subsequently, the mixture now free of air can be transferred back into the front compartment of the by-pass cartridge and the mixture will undergo a "shearing" action when passing through the passageway within the piercing member. This continued transfer from the by-pass cartridge to the syringe can be continued until the desired homogeneity of the mixture or suspension is achieved.

BRIEF DESCRIPTION OF THE DRAWINGS

Having thus generally described the invention, reference will be made to the accompanying drawings, in which.

DETAILED DESCRIPTION OF THE INVENTION

Referring to the drawings in greater detail and by reference characters thereto, there is illustrated a mixing and transfer assembly generally designated by reference numeral 10.

Figure 1:
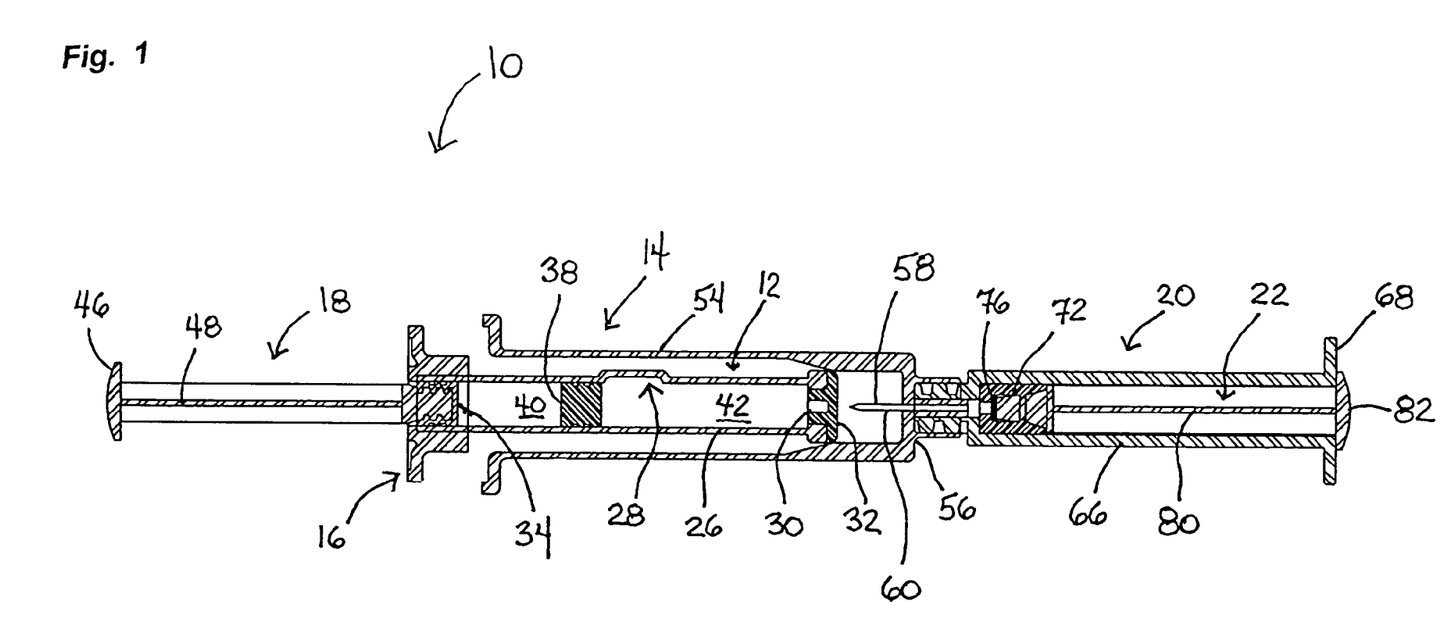
FIG. 1 is a cross-sectional view of the transfer and mixing assembly according to one embodiment of the present invention.
Figure 2:
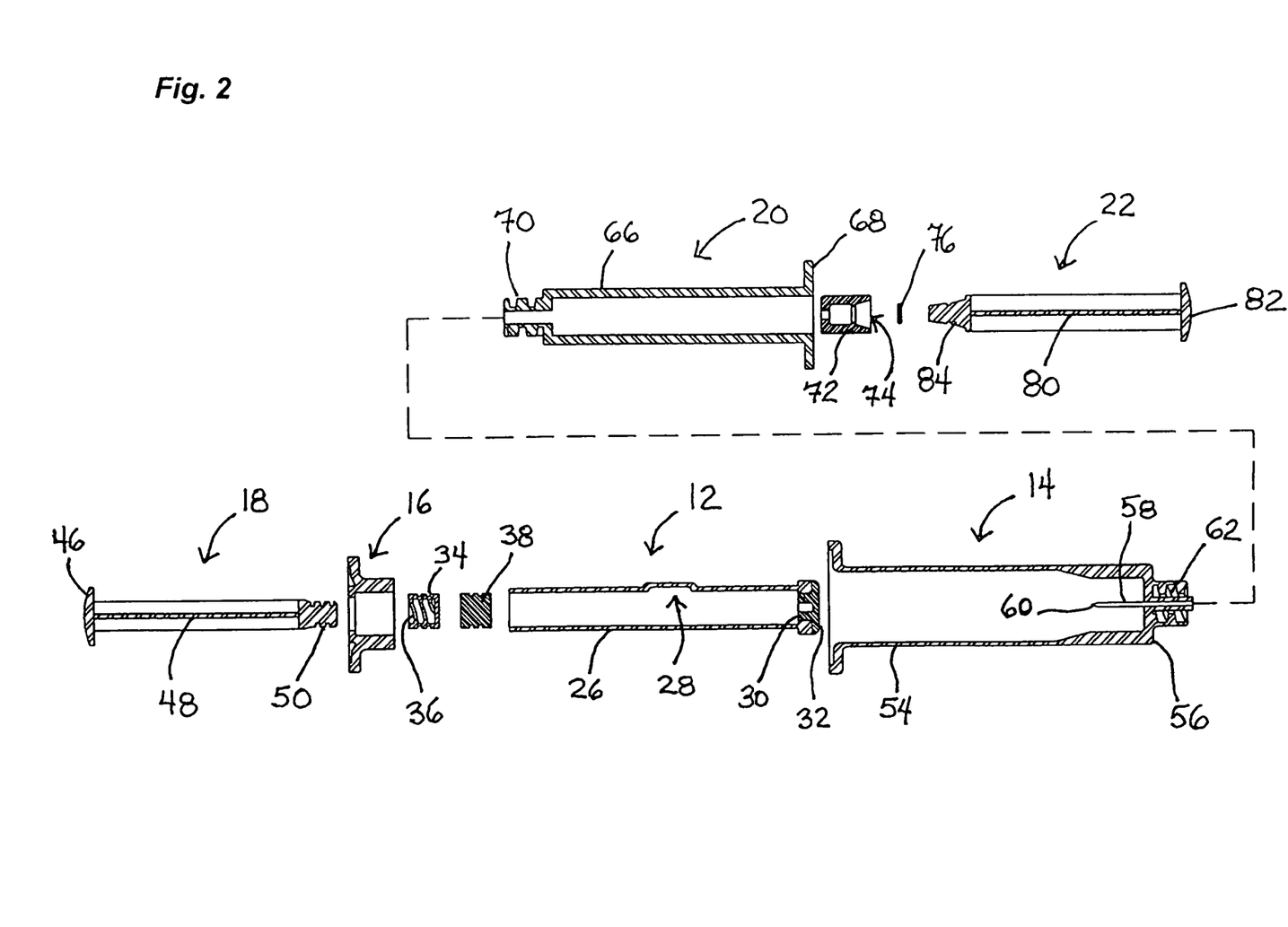
FIG. 2 is an exploded view thereof.

Transfer and mixing assembly 10 includes a by-pass cartridge generally designated by reference numeral 12, an outer housing about by-pass cartridge 12 and generally designated by reference numeral 14, an activation cap 16, a plunger rod 18, a syringe 20 and a syringe plunger rod 22.

By-pass cartridge 12 has an outer wall 26 with a by-pass 28 formed therein as is known in the art. A septum 30 covers the outlet of by-pass cartridge 12 and a cap 32 extends thereover.

Mounted within by-pass cartridge 12 is a rear plunger 34 which has a female luer fitting 36. An intermediate or middle plunger 38 is situated rearwardly of by-pass 28. There is thus formed a rear compartment 40 which is defined as the space between wall 26, rear plunger 34 and intermediate plunger 38. A front compartment 42 is defined by wall 26, intermediate plunger 38 and septum 30. For most uses, rear compartment 40 will contain the diluent while a front compartment 42 will contain the dry and active pharmaceutical component.

Plunger rod 18 includes a head 46 for ease in pushing on shaft 48. Shaft 48 is provided with a male luer fitting 50 designed to engage with luer fitting 36 on rear plunger 34.

Outer housing 54 surrounds and supports by-pass cartridge 12 and includes a side wall 54 and a top wall 56. A piercing member 58 has a bore 60 extending therethrough while an upper luer female fitting 62 is provided.

Syringe 20 includes a conventional syringe body 66 having a flange 68 at the end thereof. Syringe body 66 is provided with a luer fitting 70 designed to engage luer fitting 62 in outer housing 14. Mounted interiorly of syringe body 66 is a plunger 72 which has a passageway 74 extending therethrough. A hydrophobic membrane 76 covers passageway 74.

Syringe plunger rod 22 includes a shaft 80 having a head 82 at one end thereof and a base 84. In operation, activation cap 16 is used to push by-pass cartridge 12 forwardly such that septum 30 is pierced thereby and a fluid passageway between syringe 20 and front compartment 42 is established.

Subsequently, plunger rod 18 is attached to rear plunger 34 and pressure exerted thereon. The liquid in rear compartment 40 is substantially incompressible and accordingly, pressure is exerted on intermediate plunger 38 to move it forwardly to the area of by-pass 28. At this point, the diluent can enter into front compartment 42 to mix with the pharmaceutical component therein. A continued advancement by pressure on plunger rod 18 will cause both plungers 34, 38 to advance and air contained within front compartment 42 will pass through bore 60 of piercing member 58. The air will enter syringe body 66 and be expelled through passageway 74. In the meantime, hydrophobic membrane 76 will prevent passage of any liquid therethrough.

The continued advancement of plungers 34, 38 will force the mixture into syringe body 66 with plunger 72 being forced rearwardly. Once all the mixture has been moved to syringe body 66, plunger rod 22 may then be activated to cause the mixture to move into front compartment 42. This back and forth movement may be continued as long as needed to ensure the proper mixing of the components. The passing through bore 60 which is relatively small will ensure the mixing of the two components while preventing any foaming or air bubbles.

Preferably, plunger rod 22 is not secured to plunger 72. This will prevent any aspiration movement which would permit air to enter the mixture.

Figures 3A, 3B, 3C, 7:
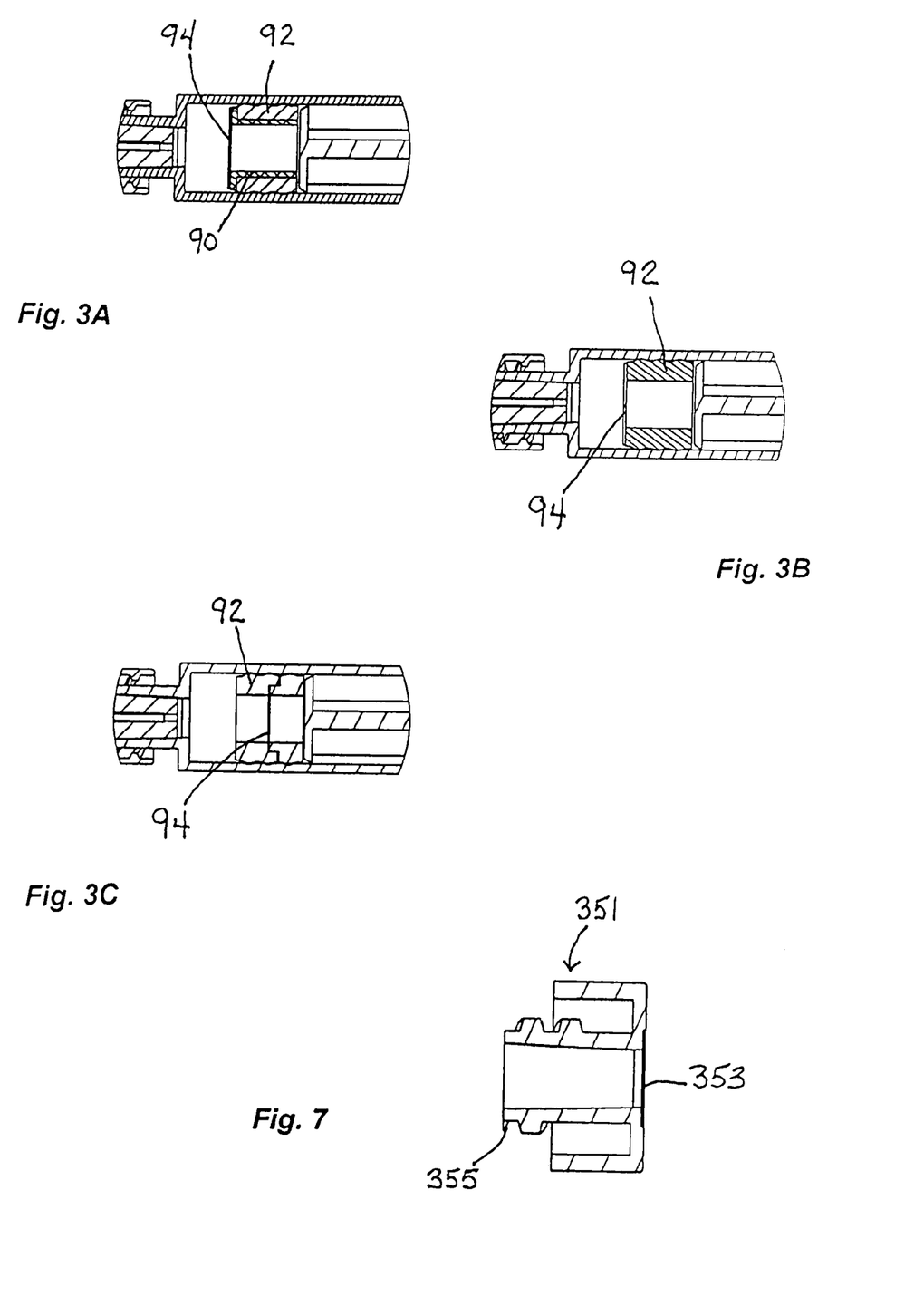
FIGS. 3A to 3C show different configurations, in cross-sections, of plungers having a hydrophobic membrane.
FIG. 7 is a sectional view of a front cap having a breathable portion thereon.

As shown in FIGS. 3A, 3B and 3C, plunger 72 may take several different forms. Thus, plunger 72 may have an insert 90 about which resilient material 92 extends. Hydrophobic membrane 94 extends across the top thereof.

In the embodiment of FIG. 2B, hydrophobic membrane 94 merely extends across resilient material 92. In the embodiment of FIG. 2C, hydrophobic membrane 94 is sandwiched between two portions of resilient material 92.

Figure 4:
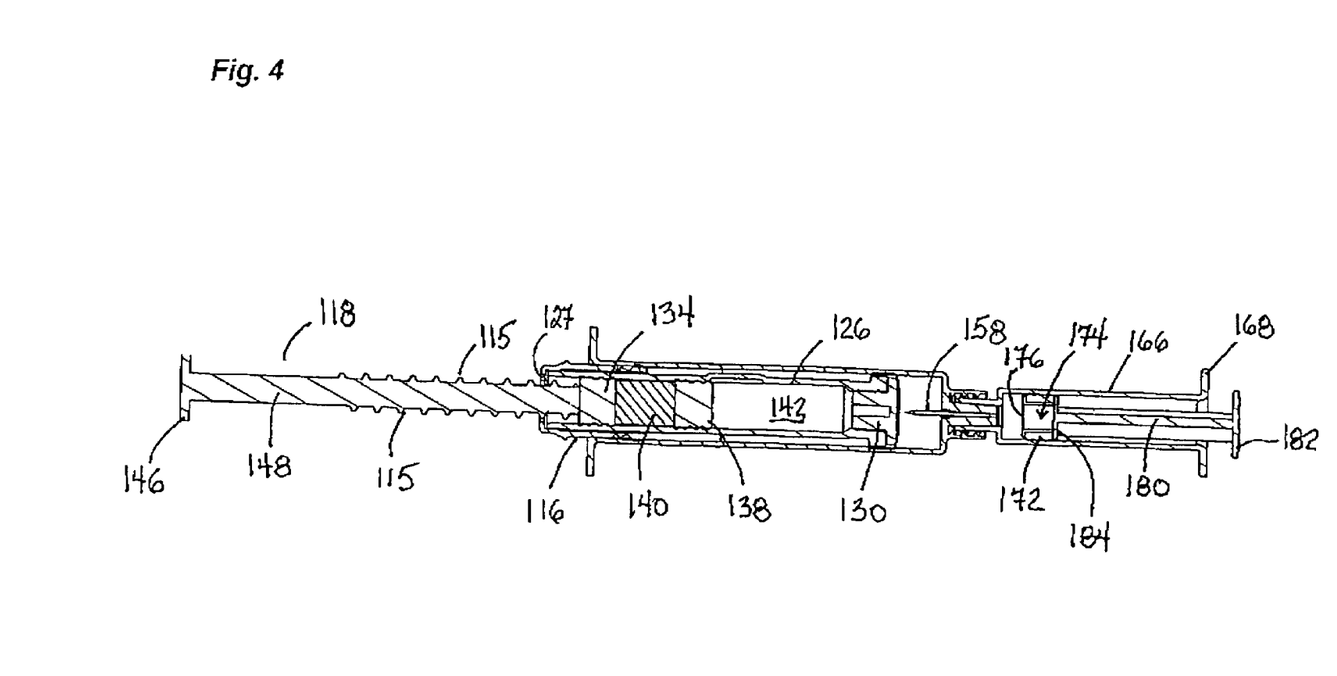
FIG. 4 is a cross-sectional view of a further embodiment of the present invention.

Turning to the embodiment of FIG. 4, there is illustrated a mixing and transferring device similar to that illustrated in FIG. 1 and similar reference numerals in the 100's are employed for similar components.

In this embodiment, plunger rod 118 has a shaft 148 with threads 115 formed on a portion thereof. Threads 115 engage with flange 127 formed on activation cap 116.

This arrangement permits a relatively slow movement of the plungers as the initial movement is dependent on the turning of plunger rod 118. After threads 115 have finished, a final pushing motion may be employed as in the previously described embodiment.

Figure 5:
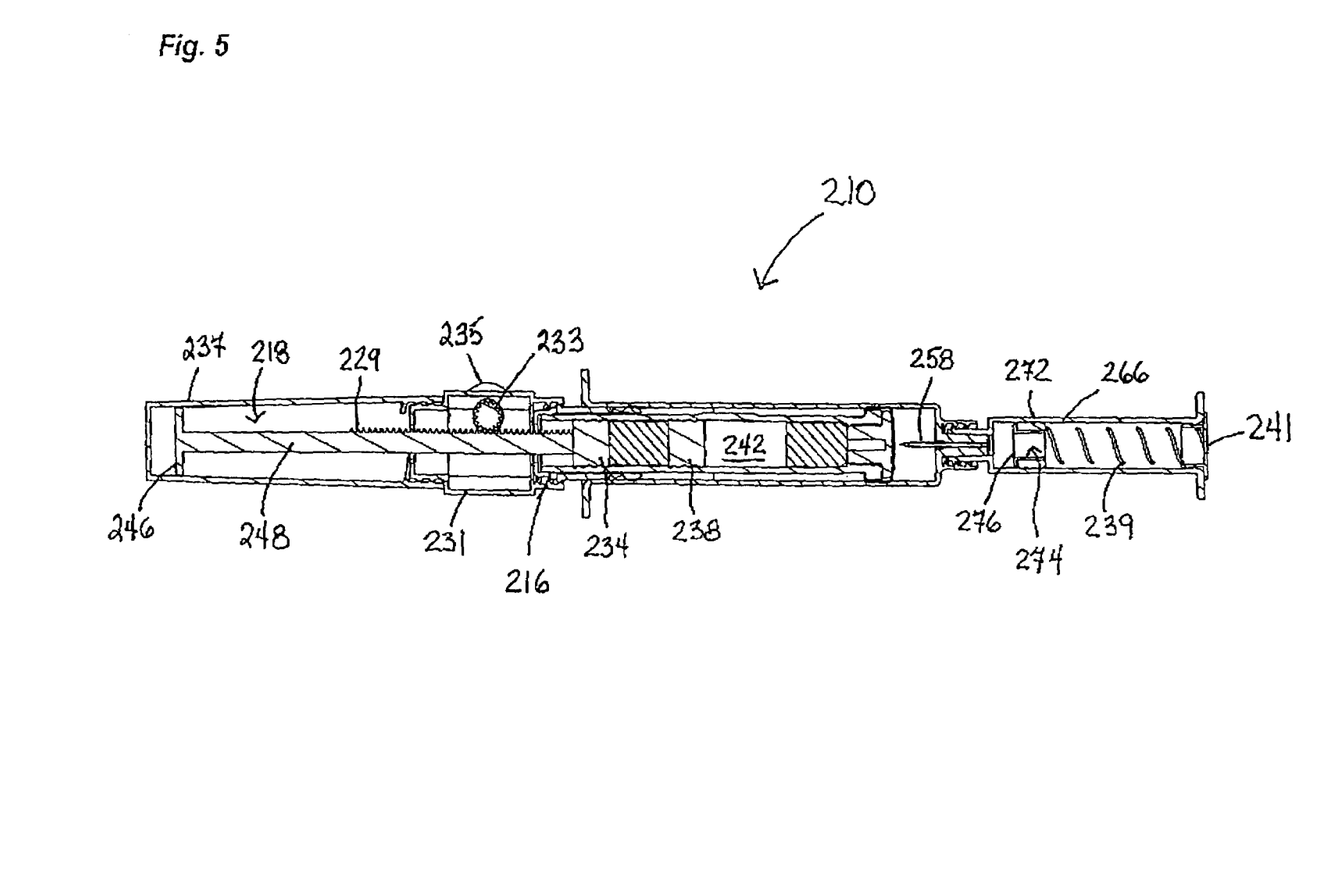
FIG. 5 is a cross-sectional view illustrating a still further embodiment of the assembly of the present invention.

In the embodiment of FIG. 5, reference numerals in the 200's are utilized for similar components.

Transfer and mixing device 210 includes a plunger rod 248 which has a plurality of teeth 229 formed on one side thereof.

A housing 231 is secured to activation cap 216. Housing 231 includes a rotatable pinion 233 by means of a thumb wheel 235. Thus, movement of thumb wheel 235 will drive plunger rod 218 in a manner previously described.

A cap 237 is mounted about plunger rod 218 and may be removed for a final pushing action thereon.

Also, as will be noted in this drawing, syringe 220 has a coil spring 239 mounted therein. A cap 241 is used for covering the end of syringe body 266.

With the arrangement of FIG. 5, transfer of the mixture into syringe 220 will continue as long as pressure is exerted on plunger rod 218. Once pressure has been removed, spring 239 will bias plunger 272 and the mixture will automatically be returned to front compartment 242.

Figure 6:
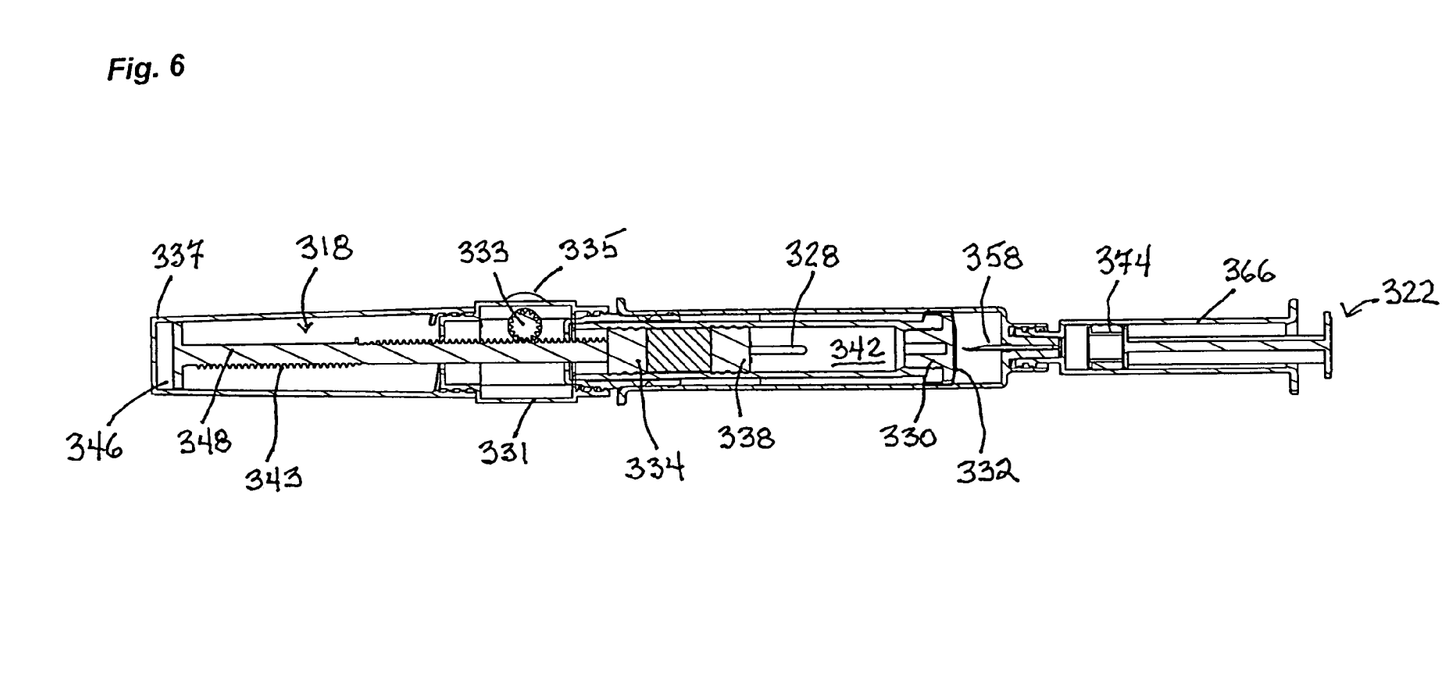
FIG. 6 is a cross-sectional view illustrating a still further embodiment of the transfer and mixing assembly.

In FIG. 6, reference numerals in the 300's are employed with similar reference numerals designating similar components. The plunger rod 318, in this embodiment, includes a plurality of teeth 343 on the end of shaft 348 proximate head 346. In this arrangement, cap 337 must be removed and plunger rod 318 rotated such that teeth 343 will then engage pinion 333.

In FIG. 7, there is illustrated a front cap which could be employed with the outer housing of the previous embodiments. Cap 351 includes a hydrophobic membrane 353 extending over an internal passageway with a male luer connection 355.

It will be understood that the above described embodiments are for purposes of illustration only and that changes and modifications may be made thereto without departing from the spirit and scope of the invention.

We claim:

1. A transfer and mixing device comprising:
   an outer housing;
   a by-pass cartridge having a by-pass formed therein, said by-pass cartridge being mounted within said outer housing;
   a septum located at a front end of said by-pass cartridge;
   a first plunger located at a rear end of said by-pass cartridge;
   a second plunger located intermediate said septum and said first plunger, said second plunger being located rearwardly of said by-pass;
   a syringe socket at a front end of said outer housing, said syringe socket including a piercing member extending inwardly towards said septum;
   a syringe securable to said syringe socket;
   a syringe plunger mounted in said syringe, said syringe plunger having a fluid passageway therein, a hydrophobic membrane covering said passageway, said passageway thereby permitting the passage of gas therethrough; and a plunger rod.

2. The transfer and mixing device of claim 1 wherein said hydrophobic membrane is formed of a polytetrafluoroethylene material.

3. The transfer and mixing device of claim 1 further including an activation cap, said activation cap being operative to advance said by-pass cartridge within said outer housing to thereby pierce said septum with said piercing member.

4. The transfer and mixing device of claim 1 further including a female luer fitting formed in said first plunger.

5. The transfer and mixing device of claim 4 wherein said plunger rod has a male luer fitting at one end thereof.

6. The transfer and mixing device of claim 1 further including a flange extending about said housing at a rear end thereof.

7. The transfer and mixing device of claim 1 further including a female luer fitting located at a front end of said outer housing.

8. The transfer and mixing device of claim 7 further including a syringe plunger rod, said syringe plunger rod being non-securable to said syringe plunger.

9. The transfer and mixing device of claim 1 wherein said plunger rod has a head portion and a shaft portion.

10. The transfer and mixing device of claim 1 wherein said plunger rod is moveable by means of a rack and pinion arrangement, a rack being formed on said plunger rod, a pinion being mounted to engage said rack.

11. The transfer and mixing device of claim 1 wherein said plunger rod has a first set of teeth formed on one side of the plunger rod and a second set of teeth formed on a second side of said plunger rod such that said plunger rod can only be advanced by said rack and pinion arrangement for a first distance using said first set of teeth and only advanced for a second distance using said second set of teeth.

12. The transfer and mixing device of claim 1 wherein said hydrophobic membrane is secured to a front face of said syringe plunger.

13. The transfer and mixing device of claim 1 wherein said hydrophobic membrane is sandwiched within said syringe plunger.

14. The transfer and mixing device of claim 1 further including a spring member located in said syringe, said spring member biasing said syringe plunger towards said syringe socket.

15. The transfer and mixing device of claim 1 further including a cap having a hydrophobic membrane.

16. The transfer and mixing device of claim 1 wherein a front compartment in said
by-pass cartridge is defined by said septum and said second plunger, said front compartment containing a dry pharmaceutical ingredient.

17. The transfer and mixing device of claim 16 wherein a rear compartment is defined by a space between said first and second plungers, said rear compartment containing a diluent.

* * * * *